United States Patent [19]

Ibanez et al.

[11] Patent Number: 4,952,206
[45] Date of Patent: Aug. 28, 1990

[54] OCCLUSION APPARATUS FOR CONVERTING A SYRINGE INTO A NON-REVERSIBLE SINGLE USE SYRINGE

[75] Inventors: Paul Ibanez, Culver City; Frederick J. Gray, Woodland Hills, both of Calif.

[73] Assignee: Anco Engineers, Inc., Culver City, Calif.

[21] Appl. No.: 354,214

[22] Filed: May 19, 1989

[51] Int. Cl.$^5$ .............................................. A61M 5/00
[52] U.S. Cl. ..................................... 604/110; 604/238
[58] Field of Search ................ 604/91, 110, 187, 199, 604/219, 236–238, 245, 256

[56] References Cited

U.S. PATENT DOCUMENTS

| | | | |
|---|---|---|---|
| 2,798,487 | 7/1957 | Ferguson | 604/238 |
| 2,893,390 | 7/1959 | Lockhart | 604/238 |
| 3,373,743 | 3/1968 | Safir | 604/237 |
| 3,941,128 | 3/1976 | Baldwin | 604/238 |
| 3,982,538 | 9/1976 | Sharpe | 128/276 |
| 4,233,975 | 11/1980 | Yerman | 604/236 |
| 4,449,693 | 5/1984 | Gereg | 251/149.8 |
| 4,479,801 | 10/1984 | Cohen | 604/238 |
| 4,559,983 | 12/1985 | Paoletti | 604/91 X |
| 4,731,068 | 3/1988 | Hesse | 604/110 |
| 4,781,683 | 11/1988 | Wozniak et al. | 604/110 |

*Primary Examiner*—John D. Yasko
*Assistant Examiner*—Adam J. Cermak
*Attorney, Agent, or Firm*—Thomas I. Rozsa

[57] ABSTRACT

A single use syringe wherein the essential concept is to create a valve within the orifice that leads from the drug chamber into the chamber leading to the needle. The valve consists of a conical washer supported within the chamber by inclined barbs formed on its outer perimeter. The barbs will only allow the washer to move in one direction; toward an orifice at the needle end of the chamber. Initially the washer is positioned so that it does not impede fluid flow in either direction. Engaging the washer but not attached to it is an expansion plug. The expansion plug can absorb fluid and expand to force the washer against the opening leading to the needle, to thereby occlude fluid flow. The process is slow, taking at least several minutes, thereby permitting the syringe to be used once for its intended purpose before occlusion occurs.

26 Claims, 1 Drawing Sheet

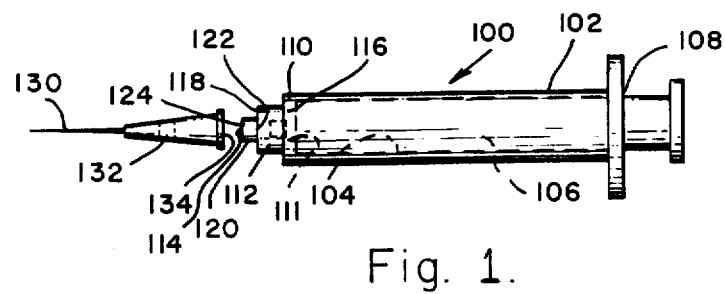
Fig. 1.
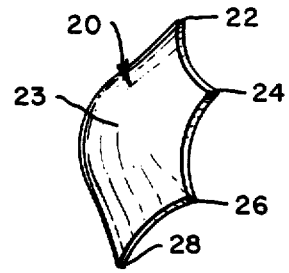
Fig. 2.
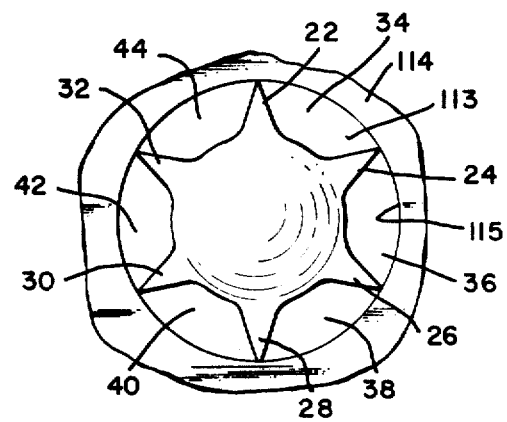
Fig. 3.
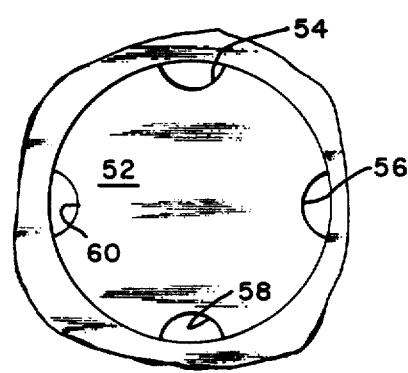
Fig. 4.
Fig. 5.
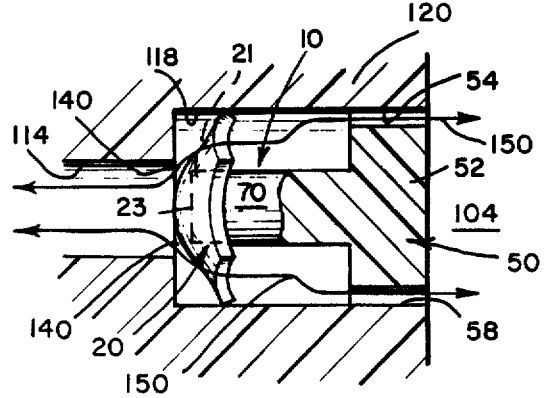
Fig. 6.
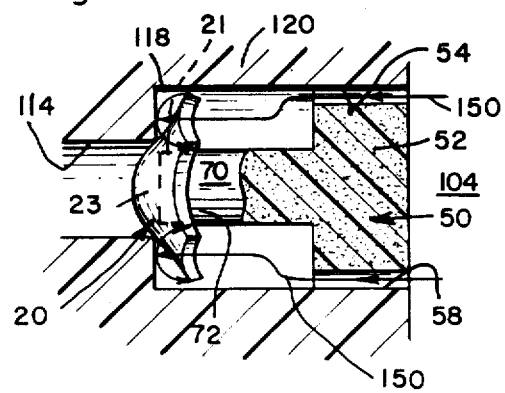
Fig. 7.

OCCLUSION APPARATUS FOR CONVERTING A SYRINGE INTO A NON-REVERSIBLE SINGLE USE SYRINGE

BACKGROUND OF THE INVENTION

1. Field of the Invention

The present invention relates to the field of injection devices and in particular syringes which are used to inject drugs and other medications into patients and which may later be used by intravenous drug users. More particularly, the present invention relates to a specialized syringe which can be used only once and is thereafter self-annulling to thereby render the syringe inoperative after it has been used only once. The present invention is concerned with a self-annulling syringe which is rendered inoperative by its own action without requiring any active destruction force from the user or medical doctor. The use of such syringes is particularly valuable to reduce the opportunity for intravenous drug users to share syringe needles and thereby spread blood-transmitted infectious diseases.

2. Description of the Prior Art

AIDS is being spread by the multiple reuse of syringes. Intravenous drug users recover discarded syringes that have been used for medical purposes and reuse and share them between infected and un-infected individuals to inject drugs such as heroin. Many inventors have conceived various embodiments to syringes but only one is intended to inactivate a syringe after it has been used once. The closest prior art relating to the principals employed in the present invention are as follows:

1. U.S. Pat. No. 4,781,683 issued to Wozniak et al and assigned to Johns Hopkins University. The Patent is entitled "Single-Use, Self-Annulling Injection Syringe" and issued on Nov. 1, 1988.

2. U.S. Pat. No. 3,982,538 issued to Sharpe on Sept. 28, 1976 for "Safety Valves For Protection Against Liquid Contamination".

3. U.S. Pat. No. 3,373,743 issued to Saffir on Mar. 19, 1968 for "Disposable Hypodermic Syringe".

4. U.S. Pat. No. 3,941,128 issued to Baldwin on Mar. 2, 1976 for "Fluid Dispensing Arrangement".

5. U.S. Pat. No. 2,798,487 issued to Ferguson on July 9, 1957 for "Syringe Assembly".

6. U.S. Pat. No. 4,449,693 issued to Gereg on May 22, 1984 for "Catheter Check Valve".

7. U.S. Pat. No. 2,893,390 issued to Lockhart on July 7, 1959 for "Hypodermic Syringes".

U.S. Pat. No. 4,781,683 to Wozniak discloses a syringe which includes within it a hydrophilic expansion plug 18 that is positioned in the fluid channel of the syringe. The hydrophilic expansion plug will swell when exposed to water contained in the medication and the inventors allege that this expansion will occlude the fluid channel, thereby preventing multiple use of the syringe and needle. While the intent is to have the plug completely fill the chamber it is in, there is no assurance that the passageway to the needle will be completely occluded and therefore it may be possible to still use the syringe, although with much less drug injecting capability, even after the plug has expanded to its full volume. The inventors of the present invention have determined that it takes only one or two thousandths of an inch gap to permit medication or drugs to flow from the drug retaining chamber to the needle. While the inventors in the Wozniak patent allege that the needle was rendered inoperative after only 5 minutes (see column 4, lines 17 through 36), it is believed that in general the bulk of and hydrogel composition of the plug in Wozniak may not completely fill all of the gap area and may leave one or two thousandths of an inch which is sufficient for drugs to be injected through the needle. In addition, with time the gel will dry and will lose some of its expansion, thereby leaving open the opportunity for reversal in the process and the creation of a one or two thousandths inch gap. In addition, not all medicines are water based and the Hydrophilic Expansion Plug 18 may not swell and occlude the fluid channel when exposed to other medicine fluids such as sesame oil.

An additional problem with the Wozniak Patent is that the device is not entirely tamper proof. Referring specifically to column 4 beginning on line 37, the Patent text states "FIG. 3 is a cross-sectional view of a single use, self-annulling syringe with a separable needle body. In this embodiment, the hydrophilic expansion plug 28 is located in a separate needle body 30. A step 32 in the needle body 30 is used to secure the hydrophilic expansion plug 28. There is sufficient elasticity in the step 32 and plug 28 to enable the plug to be press fit passed the step and locked into place." However, this same apparatus permits the device to be removed from the needle and have the hydrophilic expansion plug picked out with the scraping type device so that the needle can be reused.

U.S. Pat. No. 3,373,743 to Saffir discloses a disposable hypodermic syringe which includes within it a closure member 48. Closure member 48 is essentially an elastic piece of material which is more clearly illustrated in FIGS. 3, 6 and 7. The object of the closure member 48 is to provide a blocked passage so that medication in the syringe cannot enter into the needle. The specific intent of this patent is to create a situation where medications can be placed in the syringe and then left there for a period of time since the medication will be blocked by closure member 48 and thereby be prevented from coming in contact with the needle and therefore possibly contaminating the medication and/or corroding the needle. When in use, the plunger which moves the medication further toward the closure member under pressure causes it to distort so that the medication can pass through the openings in the closure member between the radial ribs. In this case, the closure member with radial ribs serves to temporarily block the passage of medication or drugs until distorted so that fluid can pass between the ribs. This is not a single use syringe since the syringe can be used over and over again after the closure member has become distorted.

U.S. Pat. No. 2,893,390 to Lockhart relates to a Hypodermic Syringe which includes a piston plug possessing grooves. The idea of this patent is to once again have a syringe filled with medication and then stored in a manner such that the plug blocks the passage of medication to the metal needle in order that the medication will not become contaminated and so that the needle will not corrode. When in use, the plunger causes the plug to move forward so that the grooves permit the passage of medication to the needle. Once again, after the sliding partition plug 765 has been moved forward, the syringe can be used over and over again.

U.S. Pat. No. 3,941,128 to Baldwin also embodies the same concept of having a plug which blocks medication which has been placed in a pre-filled syringe from coming in contact with the needle until such time as the plunger is depressed in which case the plug is moved to an operative form so that fluid can pass to the needle.

U.S. Pat. No. 3,982,538 to Sharpe employs the concept of a safety valve in a pipette in which the valve swells up in the presence of unwanted fluid and occludes passage of liquid.

U.S. Pat. No. 2,798,487 to Ferguson and U.S. Pat. No. 4,449,693 to Gereg show various plug arrangements or check valve arrangements.

Therefore, while various devices in the form of plug or check valve members have been known to occlude passages, the prior art embodiments do not provide an entirely satisfactory solution for causing the syringe to become inoperable. The use of a plug which merely expands to a greater size does not assure that the passageway to the needle will be entirely occluded and therefore it is possible that the syringe may still be operable for multiple uses although the effectiveness of the syringe is reduced. Therefore, a significant need exists for an improved mechanism by which there is assurance that after a single use, the syringe will become completely inoperable from further use.

SUMMARY OF THE PRESENT INVENTION

The present invention involves a single use syringe wherein the essential concept is to create a valve within the orifice that leads from the drug chamber into the chamber leading to the needle or in the needle itself. The valve consists of a conical washer supported within a chamber by inclined barbs formed on its outer perimeter. The barbs will only allow the washer to move in one direction; toward an orifice at the needle end of the chamber. Initially the washer is positioned so that it does not impede fluid flow in either direction. Engaging the washer but not attached to it is a plastic rod which is rigidly supported at its other end. During an initial suction and during the injecting stroke of the syringe, air and fluid will flow freely past the conical washer as the cross-sectional area of the flow path in the locality of the orifice is much greater than the cross-sectional area of the needle. Consequently, the normal procedures for giving an injection, filling the syringe, expelling the air, and injecting the medication or drug will remain unchanged. Valve closing is accomplished by the dimensional increase of the plastic rod which will force the conical washer into contact with the orifice, where it will be retained by its inclined barbs, effectively preventing flow in either direction. The dimensional increase will occur as a result of syringe use. As a result, the expansion is certain to occlude the orifice since the washer will be up against and inside the orifice to block the passage of medication. The use of the washer to block the orifice will insure the inoperability of the syringe even if the rod should subsequently dry and lose some of its volume. The washer will still be pressed against and into the orifice leading to the needle and retained therein by the orientation of the barbs relative to the front surface, thereby assuring a non-reversible occluding apparatus and further assuring that no liquid drug can pass to the needle.

Therefore, the present invention is an occlusion apparatus to be used in conjunction with a syringe comprising a chamber which leads to the interior opening of the syringe needle, wherein the occlusion apparatus comprises: (a) a conical washer; (b) said conical washer having a front surface and a rear surface and a multiplicity of barbs which project from the periphery of the conical washer so as to incline the conical washer in the forward direction of the front surface; (c) an expandable plug member aligned with said conical washer such that a portion of the expandable plug member is placed immediately adjacent to the rear surface of said conical washer; (d) said conical washer placed into said chamber and supported against the interior wall of the chamber by said multiplicity of barbs such that the front surface of said conical washer lies adjacent the opening of said chamber leading to the needle and separated from the opening to permit the passage of fluid to flow between the opening of the chamber leading to the needle opening and the front surface of the conical washer; (e) said expandable plug member also placed into said chamber immediately behind the rear surface of the conical washer; and (f) said expandable plug member is made of fluid absorbing material which causes the expandable plug member to expand in size when it absorbs fluid; (g) whereby the flow of medication through the syringe requires the medication to come in contact with the expandable plug member and the expansion of the plug member after absorbing fluid from the medication causes the expandable plug member to push on the rear surface of the conical washer thereby forcing the conical washer into the chamber opening leading to the needle opening, thereby occluding further flow of fluid to the needle.

Defined in greater detail, the present invention is an occlusion apparatus to be used in conjunction with a syringe comprising a needle retained by a needle gripping member, a chamber leading from a medication reservoir to a neck to which the needle gripping member is attached, and fluid communication from the medication reservoir through the chamber through the neck and through the needle gripping member to the needle, wherein the occlusion apparatus comprises: (a) a conical washer; (b) said conical washer having a front surface and a rear surface and a multiplicity of barbs which project from the periphery of the conical washer so as to incline the conical washer in the forward direction of the front surface; (c) an expandable plug member aligned with said conical washer; (d) said expandable plug member further comprising a base having at least one longitudinal opening to permit the passage of fluid and a longitudinal rod portion transversely protruding from the base in the longitudinal direction, the front of end of the longitudinal rod portion being placed immediately adjacent to the rear surface of said conical washer; (e) said conical washer placed into said chamber and supported against the interior wall of the chamber by said multiplicity of barbs such that the front surface of the conical washer lies adjacent the opening of said chamber leading to the opening in said neck and separated from the opening in said neck to permit the passage of fluid to flow between the adjacent openings of the chamber and the neck and the front surface of the conical washer; (f) said expandable plug member also placed into said chamber such that the base is press fit against the interior surface of the chamber and lies adjacent the opening of the chamber leading to the medication reservoir such that at least one opening in the base is in fluid communication with the medication reservoir and the front of the longitudinal rod portion of the expandable plug member rests immediately behind the rear surface of the conical washer; and (g) said expandable plug member is made of fluid absorbing material which causes the expandable plug member to expand in size when it absorbs fluid; (h) whereby the flow of medication through the syringe requires the medication to come in contact with the expandable plug member and the expansion of the plug member after absorbing fluid from the medication causes the longitudinal rod portion of the now expanded plug member to push on the rear surface of the conical washer thereby forcing the conical washer into the chamber opening leading to the neck and into the neck, thereby occluding further flow of fluid to the needle.

It has been discovered, according to the present invention, that the combination of a conical washer and an expandable plug means which can expand by absorbing moisture from drugs or medication placed inside the chamber of a syringe leading to the needle can be used to permit the syringe to be used once and thereafter rendered inoperable through expansion of the plug means forcing the washer to occlude the syringe's orifice leading to the needle.

It has further been discovered, according to the present invention, that the use of a plastic which does not expand to full volume until a substantial period of time, for example 30 minutes, has elapsed, permits the user to fill the syringe and pretest it through ejecting air and a small amount fluid, before using the syringe. While the syringe may be reused before the plug has fully expanded, intravenous drug users are unlikely to have access to discarded legitimately used syringes until several hours or days after original use by which time annulling will have been completed.

It has additionally been discovered, according to the present invention, that if the conical washer is formed with barbs that serve to support the washer in the chamber of the syringe and further have openings between the barbs, then the medication or drug can pass through the openings between the barbs while the syringe is being loaded and during the initial use of the syringe for injecting the medication before the syringe becomes occluded.

It has also been discovered, according to the present invention, that the configuration of a conical washer having barbs at its periphery which incline the conical washer in the forward direction serve to retain the conical washer inside an orifice once it has been pushed into the orifice by an expanding plug, thereby assuring that the process will be irreversible even if the previously expanded plug should shrink after drying.

It is therefore an object of the present invention to provide a single use syringe through a mechanism that will not rely on expansion of a substance or rod alone to occlude the passageway to the needle but will instead provide a washer mechanism that will assure that the passageway to the needle will be permanently occluded.

It is a further object of the present invention to provide a mechanism by which a syringe can be filled and tested prior to use and allow the user ample time to use the syringe before the syringe becomes occluded and prevented from further use.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a side elevational view of a conventional syringe body and separable needle, illustrating the location of the present invention inside the syringe or needle.

FIG. 2 is a perspective view of the conical washer portion of the present invention.

FIG. 3 is a front elevational view of the conical washer portion of the preset invention being supported inside the chamber of a syringe.

FIG. 4 is a perspective view of the expandable plug member portion of the present invention.

FIG. 5 is a rear elevational view of the expandable plug member portion of the present invention supported inside the chamber of a syringe.

FIG. 6 is a cross sectional view of the present invention combination conical washer and expandable plug member inside the chamber of a syringe before expansion of the plug member to thereby permit fluid such as medication to flow to the needle.

FIG. 7 is a cross sectional view of the present invention combination conical washer and expandable plug member inside the chamber of a syringe after expansion of the plug member to thereby force the conical washer into the orifice leading to the needle and occlude the passageway, thereby preventing reuse of the syringe.

DETAILED DESCRIPTION OF THE PREFERRED EMBODIMENT

Although specific embodiments of the invention will now be described with reference to the drawings, it should be understood that such embodiments are by way of example only and merely illustrative of but a small number of the many specific embodiments which can represent applications of the principles of the invention. Various changes and modifications obvious to one skilled in the art to which the invention pertains are deemed to be within the spirit, scope and contemplation of the invention as further defined in the appended claims.

Referring to FIG. 1, there is shown at 100 a conventional syringe which includes a body portion 102 surrounding therein a chamber 104. A movable piston 106 is inserted into the rear opening 108 of chamber 104 and can be moved longitudinally along the chamber to cause the interior volume of chamber 104 to be increased or decreased. The chamber 104 has a front end 110 having opening 111 therethrough. The chamber 104 narrows at its front end 110 to a smaller chamber 112 which has a rear opening 116 adjoining front end 110 of chamber 104 and a front wall 118 having an opening 114 therethrough. Smaller chamber 112 connects at its front wall 118 to a neck or needle connecting section 120 which in turn has a rear opening 122 and a front opening 124. A needle 130 is inserted into a needle gripping member 132 which has a rear opening 134. The needle gripping member 132 is attached to neck or needle connecting section 120. There is fluid communication from the large chamber 104 through the smaller chamber 112 via adjacent openings 111 and 116 respectively and from smaller chamber 112 through neck 120 via adjoining openings 114 and 122 respectively. There is also fluid connection from neck 120 to needle gripping member 132 via adjacent openings 124 and 132 respectively.

The present invention syringe occlusion apparatus is a two part structure that is designed to be inserted in the smaller chamber 112 or the needle gripping member 132. The first part of the present invention syringe occlusion apparatus 10 is a conical washer 20. The conical washer 20 has a generally circular appearance when viewed from the rear and includes on its periphery or circumference a multiplicity of support members or barbs. One embodiment of the conical washer 20 as illustrated in FIG. 3 has six support members or barbs 22, 24, 26, 28, 30 and 32. The barbs protrude radially from the periphery or circumference of the conical washer 20. The barbs are also inclined away from the front face 23 of conical washer 20, thereby orienting and pushing the conical washer 20 in the forward direction. In the preferred embodiment, the barbs are configured to the chamber of the specific syringe for which they will be used such that the barbs contact the interior circumference of the chamber and serve to support the conical washer 20 in an erect position. Referring to FIG. 3, the conical washer 20 is placed within the chamber 112 and rests inside chamber interior 113 such that the multiplicity of support members or barbs 22, 24, 26, 28, 30 and 32 contact the interior chamber wall 115 at their respective tips. In their expanded position, it is readily apparent that an opening exists between adjacent support members or barbs. In the embodiment of FIG. 3, opening 34 is located between barbs 22 and 24; opening 36 is located between barbs 24 and 26; opening 38 is located between barbs 26 and 28; opening 40 is located between barbs 28 and 30; opening 42 is located between barbs 30 and 32; and opening 44 is located between barbs 32 and 22. It will be appreciated that any multiplicity of support members or barbs can be designed into the specific conical washer and the diameter of the cross-section of the conical washer and barbs can be sized to fit the specific chamber. Referring to FIG. 6, the preferred location of the conical washer is at the forward end 118 of chamber 112 immediately in front of the opening 114 to needle attachment section or neck 120. The conical washer 20 can be made out of any suitable material such as stainless steel.

Referring to FIG. 4, the second portion of the present invention occlusion apparatus is an expandable plug member 50. The expandable plug member 50 has a base 52 which includes a multiplicity of longitudinal openings extending for the length of the base 52. In the illustration in FIG. 4, there are four longitudinal openings 54, 56, 58 and 60 which are configured as half cylinders opening out of the circumference 62 of base 52. While the openings can also extend through the body of the base, the preferred location is opening out of the circumference in order to facilitate ease of manufacturing and operability. It will be appreciated that the base can comprise at least one such opening or any multiplicity of such openings. The expandable plug member 50 further comprises a body portion 70 attached to and extending longitudinally from the base 52. The expandable plug member 50 is configured to the size of the interior 113 of chamber 112 into which it will be inserted such that the diameter of the base 52 forms a press fit within the chamber such that the circumference 62 of base 52 is flush with the interior surface wall 115. As a result, the multiplicity of openings 54, 56, 58 and 60 form longitudinal passageways between the a portion of the base 52 and the interior wall 115 of smaller chamber 112. Referring to FIG. 6, the expandable plug member 52 is inserted into the interior 113 of chamber 112 such that the front 72 of body portion 70 lies adjacent to the rear surface 21 of conical washer 20. The base 52 is press fit against the interior wall 115 of smaller chamber 114 and held therein.

It is well known that all plastics are hygroscopic to some extent and absorb water and other fluids and as a result increase in dimensions. The hygroscopic growth occurs over a time period after the plastic is subjected to moisture. The expandable plug member 50 will be made of a hygroscopic plastic material to facilitate its absorption of moisture from the drug or other medication and therefore cause its expansion. An example of such a plastic is Type 6 nylon which will absorb approximately 1.6% of its volume of water in a 24 hour period. It is inert to biological attack and resists a wide spectrum of chemicals. Other plastic materials are available that will double in size from liquid absorption in this period. Therefore, plastic with high hygroscopic expansion is the preferred material for the plug. Typically syringe bodies are made of polypropelene which has a high resistance to moisture absorption so that the majority of the liquid will be absorbed into the rod.

As illustrated in FIG. 6, in its open or unused position, the present invention occlusion apparatus 10 is situated within the interior 113 smaller chamber 112 such that a gap or opening 140 exists between the front surface 23 of conical washer 20 and the interior orifice 122 of needle attachment section or neck 120. Therefore, as illustrated in FIG. 6 by fluid flow lines 150, fluid such as medication or drugs can pass between the front 23 of conical washer 20 and into and through needle attachment section 120 and through needle gripping member 132 to the needle 130. In addition, the fluid can also pass through openings 54, 56, 58 and 60 of the base 52 and into the larger chamber 104 into which the medication or drug is drawn and held until it is ready to be injected into the patient or user.

After the medication is drawn into the syringe, the liquid from the medication begins to be absorbed by the plastic expandable plug member 50. The material is selected such that growth is not rapid and may take at least 5 minutes or more and preferably one-half hour to an hour until the plug member has reached its full size. This will give the user opportunity to test the needle to clear it of air and to be sure it squirts properly and also use the syringe to inject the medication or drug into the patient.

Referring to FIG. 7, as the expandable plug member expands, the front 72 of body portion 70 pushes on the rear 21 of conical washer 20 thereby causing the front surface 23 of conical washer 20 into the orifice 122 of the interior of needle attachment section 120, and occluding the flow of fluid therethrough. Therefore, the conical washer 20 has been forced into the narrow opening 122 in the needle attachment section or neck 120 of the syringe, thereby completely preventing the flow of fluid to or from the needle 130. The orientation of the inclined attachment members or barbs causes the conical washer 20 to only move in the forward direction into the orifice 122 and further prevents the conical washer from moving in the reverse direction out of the orifice, even if the pressure from the expandable plug member 70 is removed. The conical washer 20 is not attached to the expandable plug member 50 and therefore the conical washer 20 will remain in place in its new location even if the expandable plug member shrinks. The major advantage of this invention over the prior art such as Wozniak U.S. Pat. No. 4,781,683 is that even if the liquid absorbed by the expandable plug member 50 should dry and the expandable plug member 50 shrink from its expanded size, the washer 20 remains plugged into the needle attachment section 120 and continues to occlude fluid flow to the needle 130. As a result, through this simple process, the present invention occlusion apparatus truly converts the syringe into a single use syringe with non-reversible occlusion, thereby preventing drug users from infecting subsequent users.

The amount of movement of the rod or expandable plug member 50 can vary. The gap between the orifice 122 and the front surface 23 of conical washer 20 need only be 0.001 to 0.002 of an inch. The amount of movement required to move the conical washer 20 into the orifice 122 and occlude the orifice 122 could be in the range of 0.005 to 0.008 inch, which by way of example could be a 5% growth in the expandable plug member due to moisture absorption. By way of example, in a standard 5 cc syringe, the interior 113 of smaller chamber 112 is approximately 0.125 inch in diameter by 0.156 inch long. The entire occlusion apparatus 10 is designed to fit within this chamber without initially causing occlusion.

While the location of the occlusion apparatus 10 has been described as being inside the smaller chamber 112, it will be appreciated that the same apparatus can be modified to fit other types of syringe configurations. The principal is that the two part occlusion apparatus consisting of a conical washer which can move only in one direction and an expandable plug member pushing on the washer as it expands can be incorporated into other suitable locations in syringes or in the needle of different design to serve the same purpose, namely to have the washer embedded inside an orifice leading to the needle and thereby prevent re-use of the syringe since no fluid can pass to or through the needle.

Another advantage of the present invention is that the occlusion apparatus 10 is essentially tamper proof. It is not possible to remove the occlusion apparatus without breaking the entire syringe and therefore making it ineffective. This is a significant advantage over prior art devices which may provide some occlusion but also can be tampered with by a desperate drug addict seeking to reuse the syringe.

When placed in a syringe, the present invention converts the syringe into a single use syringe comprising: (a) a needle retained by a needle gripping member; (b) a neck to which the needle gripping member is attached; (c) a reservoir chamber for removably retaining a fluid; (d) a chamber having openings at both ends, with one end in fluid communication with said reservoir chamber and the other end in fluid communication with said neck to thereby provide fluid communication from said reservoir chamber through said chamber through said neck through said needle gripping member to said needle; (e) a conical washer; (f) said conical washer having a front surface and a rear surface and a multiplicity of barbs which project from the periphery of the conical washer so as to incline the conical washer in the forward direction of the front surface; (g) an expandable plug member aligned with said conical washer; (h) said expandable plug member further comprising a base having at least one longitudinal opening to permit the passage of fluid and a longitudinal rod portion transversely protruding from the base in the longitudinal direction, the front of end of the longitudinal rod portion being placed immediately adjacent to the rear surface of said conical washer; (i) said conical washer placed into said chamber and supported against the interior wall of the chamber by said multiplicity of barbs such that the front surface of the conical washer lies adjacent the opening of said chamber leading to the opening in said neck and separated from the opening in said neck to permit the passage of fluid to flow between the adjacent openings of the chamber and the neck and the front surface of the conical washer; (j) said expandable plug member also placed into said chamber such that the base is press fit against the interior surface of the chamber and lies adjacent the opening of the chamber leading to the fluid reservoir chamber such that said at least one opening in the base is in fluid communication with the fluid reservoir chamber and the front of the longitudinal rod portion of the expandable plug member rests immediately behind the rear surface of the conical washer; and (k) said expandable plug member is made of fluid absorbing material which causes the expandable plug member to expand in size when it absorbs fluid; (l) whereby the flow of fluid through the syringe requires the fluid to come in contact with the expandable plug member and the expansion of the plug member after absorbing fluid causes the longitudinal rod portion of the now expanded plug member to push on the rear surface of the conical washer thereby forcing the conical washer into the chamber opening leading to the neck and into the neck, thereby occluding further flow of fluid to the needle.

Defined more broadly, when placed in a syringe, the present invention converts the syringe into a single use syringe comprising: (a) a reservoir chamber for removably retaining a fluid; (b) a chamber in fluid communication with said reservoir chamber; (c) said chamber in fluid communication with the needle of said syringe; (d) a conical washer; (e) said conical washer having a front surface and a rear surface and a multiplicity of barbs which project from the periphery of the conical washer so as to incline the conical washer in the forward direction of the front surface; (f) an expandable plug member aligned with said conical washer such that a portion of the expandable plug member is placed immediately adjacent to the rear surface of said conical washer; (g) said conical washer placed into said chamber and supported against the interior wall of the chamber by said multiplicity of barbs such that the front surface of said conical washer lies adjacent the opening of said chamber leading to the needle and separated from the opening to permit the passage of fluid to flow between the opening of the chamber leading to the needle opening and the front surface of the conical washer; (h) said expandable plug member also placed into said chamber immediately behind the rear surface of the conical washer; and (i) said expandable plug member is made of fluid absorbing material which causes the expandable plug member to expand in size when it absorbs fluid; (j) whereby the flow of fluid through the syringe requires the fluid to come in contact with the expandable plug member and the expansion of the plug member after absorbing fluid from the medication causes the expandable plug member to push on the rear surface of the conical washer thereby forcing the conical washer into the chamber opening leading to the needle opening, thereby occluding further flow of fluid to the needle.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the invention might be embodied or operated.

The invention has been described in considerable detail in order to comply with the patent laws by providing full public disclosure of at least one of its forms. However, such detailed description is not intended in any way to limit the broad features or principles of the invention, or the scope of patent monopoly to be granted.

What is claimed is:

1. An occlusion apparatus to be used in conjunction with a syringe, said syringe having a chamber which leads to the interior opening of the syringe needle, wherein the occlusion apparatus comprises:
   a. a conical washer;
   b. said conical washer having a front surface and a rear surface and a multiplicity of barbs which project from the periphery of the conical washer so as to incline the conical washer in the direction of the front surface of said washer;
   c. an expandable plug member aligned with said conical washer such that a portion of the expandable plug member is placed immediately adjacent to the rear surface of said conical washer;
   d. said conical washer placed into said chamber and supported against the interior wall of the chamber by said multiplicity of barbs such that the front surface of said conical washer lies adjacent the opening of said chamber leading to the needle and separated from the opening to permit the passage of fluid to flow between the opening of the chamber leading to the needle opening and the front surface of the conical washer;
   e. said expandable plug member also placed into said chamber immediately adjacent the rear surface of the conical washer; and
   f. said expandable plug member is made of fluid absorbing material which causes the expandable plug member to expand in size when it absorbs fluid;
   g. whereby the flow of medication through the syringe requires the medication to come in contact with the expandable plug member and the expansion of the plug member after absorbing fluid from the medication causes the expandable plug member to push on the rear surface of the conical washer thereby forcing the conical washer into the chamber opening leading to the needle opening, thereby occluding further flow of fluid to the needle.

2. An occlusion apparatus in accordance with claim 1 wherein said conical washer is made of stainless steel.

3. An occlusion apparatus in accordance with claim 1 wherein said expandable plug member is made of plastic with high hygroscopic expansion.

4. An occlusion apparatus in accordance with claim 1 wherein said expandable plug member further comprises a base defining a longitudinal axis, said base having at least one longitudinal opening to permit the passage of fluid and a longitudinal rod portion transversely protruding from the base in the longitudinal direction, said rod having a rear end attached to said base, said rod having a front end on the end opposite said rear end, the front end of the longitudinal rod portion being placed immediately adjacent to the rear surface of said conical washer and said expandable plug member is placed into said chamber such that the base is press fit against the interior surface of the chamber and the front of the longitudinal rod portion of the expandable plug member rests immediately behind the rear surface of the conical washer.

5. An occlusion apparatus in accordance with claim 4 wherein said at least one longitudinal opening in said base extends longitudinally along the outer surface of the base.

6. An occlusion apparatus in accordance with claim 4 further comprising a multiplicity of spaced apart longitudinal openings in said base.

7. An occlusion apparatus in accordance with claim 6 wherein each of said multiplicity of spaced apart longitudinal openings in said base the extends longitudinally along the outer surface of said base.

8. An occlusion apparatus to be used in conjunction with a syringe, said syringe having a needle retained by a needle gripping member, a chamber leading from a medication reservoir to a neck to which the needle gripping member is attached, and fluid communication from the medication reservoir through the chamber through the neck and through the needle gripping member to the needle, wherein the occlusion apparatus comprises:
   a. a conical washer;
   b. said conical washer having a front surface and a rear surface and a multiplicity of barbs which project from the periphery of the conical washer so as to incline the conical washer in the direction of the front surface;
   c. an expandable plug member aligned with said conical washer;
   d. said expandable plug member further comprising a base defining a longitudinal axis, said base having at least one longitudinal opening to permit the passage of fluid and a longitudinal rod portion transversely protruding from the base in the longitudinal direction, said rod having a rear end attached to said base, said rod having a front end on the end opposite said rear end, the front end of the longitudinal rod portion being placed immediately adjacent to the rear surface of said conical washer;
   e. said conical washer placed into said chamber and supported against the interior wall of the chamber by said multiplicity of barbs such that the front surface of the conical washer lies adjacent the opening of said chamber leading to the opening in said neck and separated from the opening in said neck to permit the passage of fluid to flow between the adjacent openings of the chamber and the neck and the front surface of the conical washer;
   f. said expandable plug member also placed into said chamber such that the base is press fit against the interior surface of the chamber and lies adjacent the opening of the chamber leading to the medication reservoir such that said at least one opening in the base is in fluid communication with the medication reservoir and the front of the longitudinal rod portion of the expandable plug member rests immediately adjacent the rear surface of the conical washer; and
   g. said expandable plug member is made of fluid absorbing material which causes the expandable plug member to expand in size when it absorbs fluid;
   h. whereby the flow of medication through the syringe requires the medication to come in contact with the expandable plug member and the expansion of the plug member after absorbing fluid from the medication causes the longitudinal rod portion of the now expanded plug member to push on the rear surface of the conical washer thereby forcing the conical washer into the chamber opening leading to the neck and into the neck, thereby occluding further flow of fluid to the needle.

9. An occlusion apparatus in accordance with claim 8 wherein said conical washer is made of stainless steel.

10. An occlusion apparatus in accordance with claim 8 wherein said expandable plug member is made of plastic with high hygroscopic expansion.

11. An occlusion apparatus in accordance with claim 8 wherein at least one longitudinal opening in said base projects out of the circumference of the base and extends along the outer surface of the base.

12. An occlusion apparatus in accordance with claim 8 further comprising a multiplicity of spaced apart longitudinal openings in said base.

13. An occlusion apparatus in accordance with claim 12 wherein each of said multiplicity of spaced apart longitudinal openings in said base extends longitudinally along the outer surface of said base.

14. A single use syringe having a needle comprising:
   a. a reservoir chamber for removably retaining a fluid;
   b. a chamber in fluid communication with said reservoir chamber;
   c. said chamber in fluid communication with the needle of said syringe;
   d. a conical washer;
   e. said conical washer having a front surface and a rear surface and a multiplicity of barbs which project from the periphery of the conical washer so as to incline the conical washer in the direction of the front surface of said washer;
   f. an expandable plug member aligned with said conical washer such that a portion of the expandable plug member is placed immediately adjacent to the rear surface of said conical washer;
   g. said conical washer placed into said chamber and supported against the interior wall of the chamber by said multiplicity of barbs such that the front surface of said conical washer lies adjacent the opening of said chamber leading to the needle and separated from the opening to permit the passage of fluid to flow between the opening of the chamber leading to the needle opening and the front surface of the conical washer;
   h. said expandable plug member also placed into said chamber immediately adjacent the rear surface of the conical washer; and
   i. said expandable plug member is made of fluid absorbing material which causes the expandable plug member to expand in size when it absorbs fluid;
   j. whereby the flow of fluid through the syringe requires the fluid to come in contact with the expandable plug member and the expansion of the plug member after absorbing fluid from the medication causes the expandable plug member to push on the rear surface of the conical washer thereby forcing the conical washer into the chamber opening leading to the needle opening, thereby occluding further flow of fluid to the needle.

15. A syringe in accordance with claim 14 wherein said conical washer is made of stainless steel.

16. A syringe in accordance with claim 14 wherein said expandable plug member is made of plastic with high hygroscopic expansion.

17. A syringe in accordance with claim 14 wherein said expandable plug member further comprises a base defining a longitudinal axis, said base having at least one longitudinal opening to permit the passage of fluid and a longitudinal rod portion transversely protruding from the base in the longitudinal direction, said rod having a rear end attached to said base, said rod having a front end on the end opposite said rear end, the front end of the longitudinal rod portion being placed immediately adjacent to the rear surface of said conical washer and said expandable plug member is placed into said chamber such that the base is press fit against the interior surface of the chamber and the front of the longitudinal rod portion of the expandable plug member rests immediately behind the rear surface of the conical washer.

18. An occlusion apparatus in accordance with claim 17 wherein said at least one longitudinal opening in said base extends longitudinally along the outer surface of the base.

19. An occlusion apparatus in accordance with claim 14 further comprising a multiplicity of spaced apart longitudinal openings in said base.

20. An occlusion apparatus in accordance with claim 19 wherein each of said multiplicity of spaced apart longitudinal openings in said base extends longitudinally along the outer surface of said base.

21. A single use syringe comprising:
   a. a needle retained by a needle gripping member;
   b. a neck to which the needle gripping member is attached;
   c. a reservoir chamber for removably retaining a fluid;
   d. a chamber have openings at both ends, with one end in fluid communication with said reservoir chamber and the other end in fluid communication with said neck to thereby provide fluid communication from said reservoir chamber through said chamber through said neck through said needle gripping member to said needle;
   e. a conical washer;
   f. said conical washer having a front surface and a rear surface and a multiplicity of barbs which project from the periphery of the conical washer so as to incline the conical washer in the direction of the front surface of said washer;
   g. an expandable plug member aligned with said conical washer;
   h. said expandable plug member further comprising a base defining a longitudinal axis, said base having at least one longitudinal opening to permit the passage of fluid and a longitudinal rod portion transversely protruding from said rod having a rear end attached to said base, said rod having a front end on the end opposite said rear end, the base in the longitudinal direction, the front end of the longitudinal rod portion being placed immediately adjacent to the rear surface of said conical washer;
   i. said conical washer placed into said chamber and supported against the interior wall of the chamber by said multiplicity of barbs such that the front surface of the conical washer lies adjacent the opening of said chamber leading to the opening in said neck and separated from the opening in said neck to permit the passage of fluid to flow between the adjacent openings of the chamber and the neck and the front surface of the conical washer;
   j. said expandable plug member also placed into said chamber such that the base is press fit against the interior surface of the chamber and lies adjacent the opening of the chamber leading to the fluid reservoir chamber such that said at least one opening in the base is in fluid communication with the fluid reservoir chamber and the front of the longitudinal rod portion of the expandable plug member rests immediately behind the rear surface of the conical washer; and k. said expandable plug member is made of fluid absorbing material which causes the expandable plug member to expand in size when it absorbs fluid;

l. whereby the flow of fluid through the syringe requires the fluid to come in contact with the expandable plug member and the expansion of the plug member after absorbing fluid causes the longitudinal rod portion of the now expanded plug member to push on the rear surface of the conical washer thereby forcing the conical washer into the chamber opening leading to the neck and into the neck, thereby occluding further flow of fluid to the needle.

22. A syringe in accordance with claim 21 wherein said conical washer is made of stainless steel.

23. A syringe in accordance with claim 21 wherein said expandable plug member is made of plastic with high hygroscopic expansion.

24. A syringe in accordance with claim 21 wherein said at least longitudinal opening in said base extends longitudinally along the outer surface of the base.

25. An occlusion apparatus in accordance with claim 21 further comprising a multiplicity of spaced apart longitudinal openings in said base.

26. An occlusion apparatus in accordance with claim 25 wherein each of said multiplicity of spaced apart longitudinal openings in said base extends longitudinally along the outer surface of said base.

* * * * *